(12) United States Patent
Albrecht

(10) Patent No.: US 6,763,728 B1
(45) Date of Patent: Jul. 20, 2004

(54) EVALUATION OF BURST TEST RESULTS

(75) Inventor: Mark Christopher Albrecht, Chanhassen, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 512 days.

(21) Appl. No.: 09/697,943

(22) Filed: Oct. 26, 2000

(51) Int. Cl.[7] .............................................. G01N 3/00
(52) U.S. Cl. ...................................................... 73/838
(58) Field of Search ......................... 73/826, 827, 831, 73/838, 839, 840

(56) References Cited

U.S. PATENT DOCUMENTS

| | | | | |
|---|---|---|---|---|
| 5,411,497 A | * | 5/1995 | Tanzer et al. | 604/368 |
| 5,593,399 A | * | 1/1997 | Tanzer et al. | 604/368 |
| 5,958,531 A | * | 9/1999 | Stevenson | 428/35.8 |
| 6,478,264 B1 | * | 11/2002 | Nelson et al. | 248/65 |

* cited by examiner

*Primary Examiner*—Max Noori
(74) *Attorney, Agent, or Firm*—INCAPLAW; Terrance A. Meador

(57) ABSTRACT

A method for evaluating a seal on a package is disclosed. The method includes determining the value of a burst test force parameter. The burst test force parameter being a parameter that results from a force placed on the package during a burst test. The method also includes using the value of the burst test force parameter to determine a value of a peel test force parameter for the package. The peel test force parameter being a parameter that results from a force placed on the package during a peel test.

34 Claims, 6 Drawing Sheets

ASSOCIATED WITH A
PARTICULAR PACKAGE
AND SEAL TYPE

EVALUATION OF BURST TEST RESULTS

BACKGROUND

1. Field of the Invention

The invention relates generally to testing of packaging seals. More specifically, the invention relates to evaluation of seal testing results.

2. Background of the Invention

The packaging of sterile products such as medical devices must be manufactured according to strict specifications in order to prevent contamination of the product. The packaging for these products often includes one or more seals where portions of the packaging are bonded. A variety of specifications and regulations are directed toward the integrity of these seals. As a result, the manufacturers and users of this packaging often must have access to technology for testing these seals.

There are a variety of methods and devices available for testing packaging seals. The two most common are peel testing and burst testing. Peel testing is performed by cutting the package into a several pieces that each have a portion of the seal. The seal on each piece is pulled apart at a constant velocity while measuring the force on the seal. Peel testing is known to provide reliable seal integrity results. However, because the packaging must be cut into several pieces that are each tested independently, evaluating the integrity of the seal on a single packaging can take a long time. Additionally, the testing can miss the weakest part of the seal.

Burst testing includes inflating the packaging with a fluid until the seal bursts. The most common methods involve recording the maximum pressure reached before the package seal ruptures. Although burst testing has proven to be a quicker test, the results are often unreliable. Additionally, there is currently not a reliable method available for comparing burst test results with peel test results. For the above reasons, there is a need for a reliable burst test and a need for a method of processing the results so they can be compared with peel test results.

SUMMARY OF THE INVENTION

The invention relates to a method for evaluating a seal on a package. The method includes determining the value of a burst test force parameter. The burst test force parameter being a parameter that results from a force placed on the package during a burst test. The method also includes using the value of the burst test force parameter to determine a value of a peel test force parameter for the package. The peel test force parameter being a parameter that results from a force placed on the package during a peel test.

Another embodiment of the method includes using the value of the burst test force parameter to determine a seal integrity. The seal integrity is a value that is determined using a peel test under specific parameters to evaluate the quality of the seal. Because the peel test seal integrity is determined using a peel test, the method allows burst test results to be converted to a seal integrity value that can be compared with the seal integrity values that are generated directly from peel tests. Hence, an embodiment of the method allows for comparison of burst test results and peel test results.

The invention also relates to data for use with a seal testing device. The data includes burst test force parameter values related to peel test force parameter values. The relation indicates the burst test force parameter value and the peel test force parameter value that would result from performing a burst test and a peel test such that a seal would peel at substantially the same velocity during the burst test and during the peel test.

The invention also relates to a database for use with a seal testing device. The database includes a plurality of burst test force parameter values and a plurality of peel test force parameter values. Each peel test force parameter value is associated with one of the burst test force parameter values. Additionally, an associated peel test force parameter value and burst test force parameter value result from a burst test and peel test performed such that a seal would peel at substantially the same velocity during the burst test and during the peel test.

Another embodiment of a database for use with a seal testing device includes a plurality of seal velocity values and a plurality of peel test force parameter values. Each peel test force parameter value is associated with one of the seal velocity values and results from performing a peel test at the associated peel velocity. In one embodiment of the invention, a plurality of these databases are each associated with a seal integrity. The plurality of databases can be arranged in a three dimensional database.

The invention also relates to a method of preparing data for use with a seal testing device. The method includes performing a burst test and a peel test such that a type of seal on a type of package peels at substantially the same velocity during the peel test and the burst test. The method also includes evaluating a burst test force parameter value that results from a force applied to the package during the burst test and evaluating a peel test force parameter value that results from a force applied to the package during the peel test. The method further includes storing the value of the burst test force parameter such that it is associated with the value of the peel test force parameter.

Another method of preparing data for use with a seal testing device includes performing a plurality of peel tests on packages that each have the same seal integrity rating. Each peel test is performed at a different peel velocity. The method also includes evaluating a peel test force parameter value resulting from each peel test. The method further includes storing the peel test force parameter values such that the peel test force parameter value for a particular peel test is associated the with the peel velocity at which the particular peel test was performed. In one embodiment of the invention, this method is repeated for packages having different seal integrities. This embodiment can further include storing the peel test force parameters and the associated peel velocities such that the peel test force parameters and the associated peel velocities are associated with a seal integrity.

DETAILED DESCRIPTION OF THE PREFERRED EMBODIMENT

Figure 1:
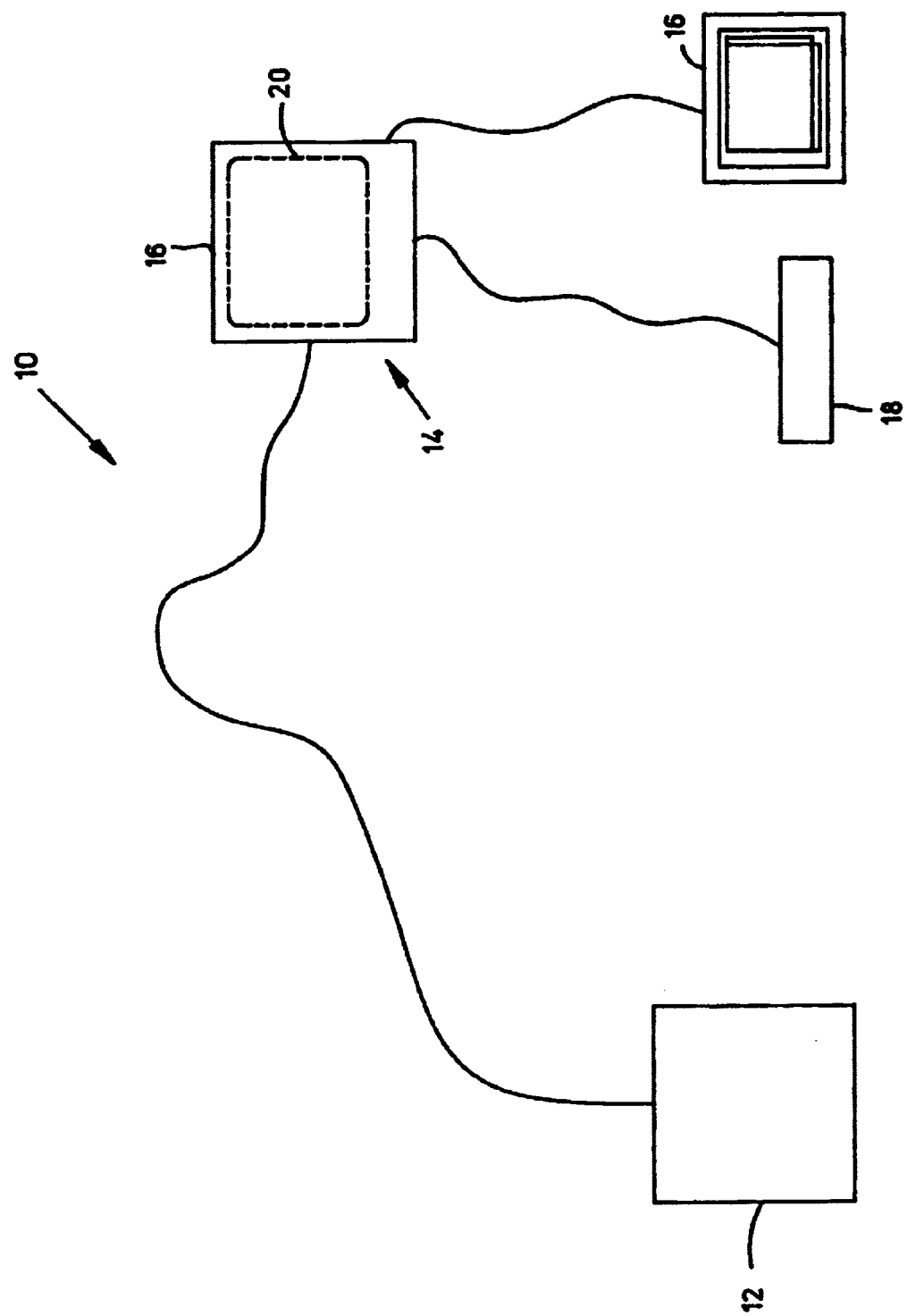
FIG. 1 illustrates a system for evaluating seal test results.

The invention relates to a system for evaluating seals on a package. A burst test is performed on the package such that the seal peels apart. The burst test can be either a restrained burst test or an unrestrained burst test and is performed such that a substantially constant pressure is maintained while the seal is peeling. The burst test is used to evaluate several parameters. Suitable parameters include, the velocity at which the seal peels and the value of one or more burst test force parameters. Burst test force parameters are parameters that result from a force being applied to the seal during the burst test. Accordingly, the value of a burst test force parameters provides information about the force applied to the seal during the burst test. For example, the average pressure within the package over the period of time required for the seal to completely peel can be evaluated.

In one embodiment of the invention, the value of a burst test force parameter is converted to a peel test force parameter value. A peel test force parameter is a parameter that result from a force being applied to the seal during a peel test. Accordingly, the value of a peel test force parameters provides information about the force applied to a seal during a peel test. For example, the average force applied to a seal over the period of time required for the seal to completely peel can be evaluated.

The burst test force parameter value is converted to a peel test force parameter value by comparing the burst test force parameter value with a test conversion relationship. A test conversion relationship associates burst test force parameter values with peel test force parameter values. The association indicates the burst test force parameter value and the peel test force parameter value that would result from performing a burst test and a peel test such that a seal would peel at substantially the same velocity during the burst test and during the peel test. Accordingly, a burst test force parameter value for a particular seal can be compared to the relationship to determine a peel test force parameter value for the seal. The resulting peel test force parameter value is the approximate value of the peel test force parameter that would result if a peel test had been performed on the seal at the peel velocity that occurred during the burst test. Hence, the resulting peel test force parameter value can be directly compared with peel test force parameter values generated from peel tests.

A method for generating a test conversion relationship includes performing a constant pressure burst-test on a package. The value of a burst test force parameter and a peel velocity are evaluated. A peel test is then performed on either an undisturbed segment of the package or on a seal that was manufactured to have a seal quality that is substantially the same as the seal of the burst package. The peel test is performed at the peel velocity that resulted during the burst test. A peel test force parameter value is evaluated during the peel test. The burst test force parameter value and the peel test force parameter value are then stored such that the burst test force parameter value is associated with the peel test force parameter value. For instance, the burst test force parameter value and the peel test force parameter value can be stored in a database that associates the burst test force parameter value with the peel test force parameter value. Because the burst test force parameter value and the associated peel test force parameter value are generated from tests performed such that the seal peeled at approximately the same peel velocity, the peel test force parameter value can be approximately determined for a package by performing a constant pressure burst test on the package and comparing the results of the burst test to the database associating burst test force parameter values with peel test force parameter values.

The system can also employ seal integrity evaluation data. A peel test force parameter value generated as described above can be compared with the seal integrity evaluation data in order to approximate the seal integrity for a package. As will be described in more detail below, the seal integrity evaluation data can be generated using peel tests. Accordingly, the approximated seal integrity can be directly compared with other integrity values resulting from peel tests. Hence, an embodiment of the invention allows burst test results to be converted to an integrity: value that can be directly compared with integrity values generated from peel tests.

FIG. 1 illustrates a system 10 for evaluating seal test results. The system 10 includes a seal testing device 12. Suitable seal testing devices include, but are not limited to, a peel testing device and a burst testing device. The system 10 also includes a processing unit 14 in communication with the seal testing device 12, a display 16 and one or more user interfaces 18. The processing unit 14 houses electronics 20 for controlling various operations of the system 10. For instance, the electronics 20 can measure one or more parameters during the testing of a package 20 by the seal testing device 12 and provide additional processing of these parameters according to the methods of the present invention. The display 16 can be used to show parameters that have been measured by the system 10.

An operator can use the one or more user interfaces 18 to interact with the system 10. For instance, the user can change what is shown on the display 16 or vary system 10 settings such as the peel velocity of a peel test or the pressure of a constant pressure burst test. A suitable user interface 18 includes, but is not limited to, a keyboard and a mouse. Although a single processing unit 14, user interfaces 18 and display 16 are illustrated, the system 10 can include a plurality of processing units 14, displays 16 and user interfaces 18. Additionally, the system 10 can include more than one seal testing device 12. For instance, the processing unit 14 can be in communication with both a seal testing device 12 and a burst testing device. The processing unit 14 can then store and process data achieved by testing on either device.

The electronics 20 can include one or more processors for performing instructions stored or carried on a machine readable medium. Suitable processors include, but are not limited to, programmed general purpose digital computers, microprocessors, digital signal processors (DSP), integrated circuits, application specific integrated circuits (ASICs), logic gate arrays and switching arrays.

Suitable machine readable media include, but are not limited to, RAM, disk drives, optical discs such as a compact disk (CD), CD-ROM, CD-R (a recordable CD-ROM that can be read on a CD-ROM drive), CD-RW (multiple-write CD), CD-E (recordable and erasable CD), or DVD (digital video disc). Alternatively, instead of, or in addition to an optical disc, the machine readable media can include one or more of the following: a magnetic data storage diskette (floppy disk), a Zip disk, DASD storage (e.g., a conventional "hard drive" or a RAID array), magnetic tape, RAM, electronic read-only memory (e.g., ROM, EPROM, or EEPROM), paper punch cards, or transmission media such as digital and/or analog communication links. In some instances, one or more of the machine readable media are positioned outside or remote from the processing unit 14. For instance, the machine readable medium may be part of, or may be connected to, a server computer that is connected to a network, to in order to make the machine-readable code available to other computers.

Figure 2A:
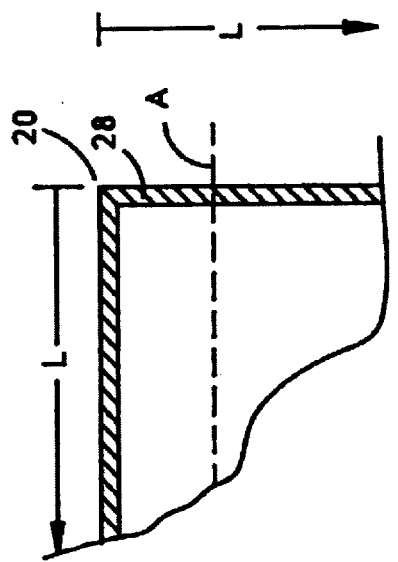
FIG. 2A is a top view of a package having a seal.
Figure 2B:
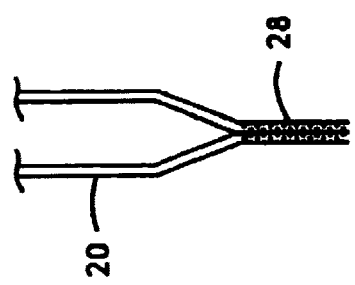
FIG. 2B is a cross sectional view of the package shown in FIG. 2A taken along the line labeled A.

FIGS. 2A–2D illustrates a package 20 having a seal 28. FIG. 2A is a top view of the package 20 while FIG. 2B is a cross sectional view of the package 20 taken along the line labeled A in FIG. 2A. The package 20 includes two pieces of material bonded together at a seal 28. The seal 28 is illustrated as a darkened area to show the bonded nature of the material. The seal length is labeled L and the seal width is labeled W.

Figure 2D:
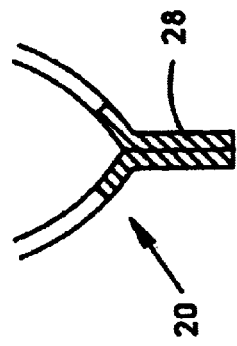
FIG. 2D illustrates the seal being peeled apart during a burst test
Figure 2C:
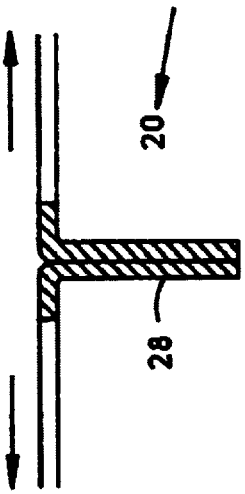
FIG. 2C illustrates a seal being peeled during a peel test.

FIG. 2C illustrates a seal 28 being peeled during a peel test. The materials are pulled in opposite directions as illustrated by the arrow labeled A. The force on the seal 28 causes the seal 28 to peel apart. The seal 28 is typically pulled apart at a constant velocity and a peel test force parameter measured as the seal 28 is peeled. A peel test force parameter is a parameter that result from a force being applied to the seal 28 during a peel test. Accordingly, the value of a peel test force parameters provides information about the force applied to a seal 28 during a peel test. Suitable peel test force parameters include, but are not limited to, force, work and power. The peel test force parameter can also be an average value such as average force during the peel of the seal 28. The peel test force parameter can also be measured in terms of length such as force per unit length or work per unit length. Additionally, the peel test force parameter can be broken down into directional components such as vertical force and/or horizontal force applied to the seal 28. The peel test force parameter can also be directed toward a feature such as a peak force or a minimum force during the peel. One peel test force parameter can be measured during the peel test and converted into another peel test force parameter after the peel test. For instance, the force can be measured as the seal 28 is peeled. The measured force can be integrated over time in order to determine an average force during the peel test. Combinations of these peel test force values can also be used.

FIG. 2D illustrates the seal 28 being peeled apart during a burst test. The seal 28 is pulled apart by the pressure within the package 20. As a result, the force on the seal 28 is not necessarily in opposing directions as it is during the peel test.

As described above, the burst test can be a performed at constant pressure. A constant pressure burst test can be accomplished with software, mechanics or combinations of both. For instance, the processing unit 14 can monitor a pressure measuring device and control the introduction of the fluid into the package 20 until a target pressure is achieved with the package 20. The processing unit 14 can control additional introductions of fluid into the package 20 to maintain the pressure at the target pressure. Alternatively, the burst testing device can include a pressure regulator that acts as a release valve when the pressure in the package 20 exceeds the target pressure. The fluid can be introduced into the package 20 at a constant rate because the pressure regulator prevents the pressure from exceeding the target pressure.

Figure 3:
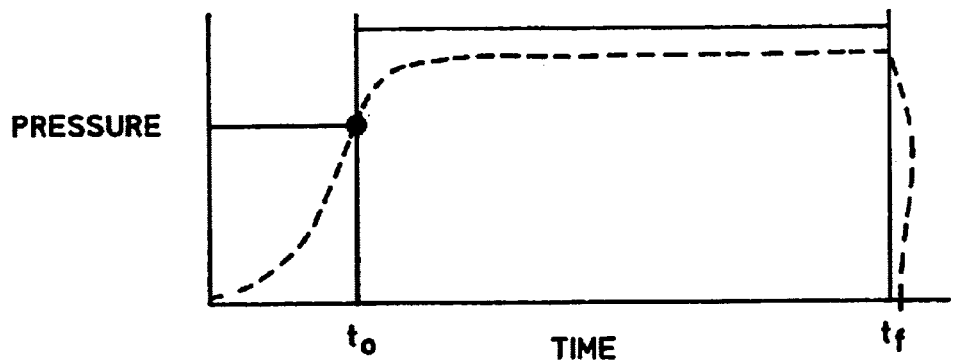
FIG. 3 illustrates a pressure profile during a constant pressure burst test.

FIG. 3 illustrates a typical profile of pressure versus time for a constant pressure burst test. A fluid is introduced into the package 20 at a rate that causes the pressure in the package 20 to quickly rise to the target pressure. The target pressure is above a pressure that causes the seal 28 to peel. The seal 28 begins to peel at the time labeled $t_0$. Shortly after the seal 28 beings to peel, the pressure within the package 20 reaches the target pressure. The seal 28 bursts at the time labeled $t_f$. The pressure drops off rapidly once the seal 28 peels far enough for the fluid to rapidly escape from the package 20.

Because the target pressure within the package 20 is above the pressure where the seal 28 begins to peel, the seal 28 begins to peel before the target pressure can be achieved. As a result, a portion of a constant pressure burst test is presumably performed with a dynamic pressure.

The constant pressure burst test is used to evaluate several parameters. A parameter that can be measured during the constant pressure burst test is the velocity at which the seal 28 peels. Applying the principles of conservation of work to a burst test and presuming a very small internal area change or that restraining plates maintain a substantially constant ratio of exposed area (area not in contact with the plates) to seal perimeter shows that when a package 20 is burst at constant pressure, the velocity that the seal 28 peels remains constant. Accordingly, the peel velocity of a seal 28 peeled under constant pressure can be determined by dividing the width of the seal 28 by the time required for the seal 28 to peel. The time for the seal 28 to peel is illustrated in FIG. 3 as the time from $t_0$ to $t_f$. This time is called the peel time below.

The processing unit 14 can measure the peel time. The value of the pressure where $t_0$ occurs can be approximated from theoretical equations that are entered into the processing unit 14. The processing unit 14 can then use these equations to find the pressure where $t_0$ occurs and start measuring time once the pressure is reached. Alternatively, $t_0$ can be experimentally determined by slowly raising the pressure in the package 20 to determine the pressure where the seal 28 begins to peel. A user interface can be used to enter this pressure into the processing unit 14. The processing unit 14 can start measuring time once the entered pressure is reached. The processing unit 14 stops measuring time upon identifying the sudden pressure drop that occurs at $t_f$.

In some embodiments, the processing unit 14 can automatically measure the seal width. For instance, the processing unit 14 can be in communication with a camera based vision system. Camera based vision systems use high resolution/high velocity video or digital cameras to take pictures of an object. Software is then used to create measurements based on a known ratio of pixels to unit of measure. These type of systems range from simple "pixel counters" that count light vs. dark pixels to systems that use more complicated algorithms to "see" fine contrast levels, faint lines, and other difficult to detect features. Lighting also plays a very important role in these systems. Color of light, polarization, filters on the cameras, etc. can all be used to enhance the seal 28 for easier observation. Alternatively, the seal width can be manually measured with an instrument such as calipers. A user interface can then be used to enter the measured seal width into the processing unit 14. The processing unit 14 can determine the average velocity that the seal 28 peels during the burst test by dividing the seal width by the peel time.

Other parameters that can be determined from the burst test include, but are not limited to, the value of one or more burst test force parameters. Burst test force parameters are parameters that result from a force being applied to the seal 28 during the burst test. Accordingly, the value of a burst test force parameters provides information about the force applied to the seal 28 during the burst test. Suitable burst test force parameters include, but are not limited to, pressure, force, work and power. The burst test force parameter can also be an average value such as average pressure during the peel of the seal 28. The burst test force parameter can also be measured in terms of length such as work per unit length. Additionally, the burst test force parameter can be broken down into directional components such as vertical force and/or horizontal force applied to the seal 28 The peel test force parameter can also be directed toward a feature such as a peak pressure and/or a minimum pressure: during the peel. One burst test force parameter can be measured during the peel test and converted into another peel test force parameter after the peel test. For instance, the pressure can be measured as the seal 28 is peeled. The measured force can then be integrated over time in order to determine an average pressure. Indirect indicators of the force applied to the seal 28 during the burst test can also be employed as the burst test force parameter. For instance, the flowrate of fluid into and/or out of the package 20 during the burst test can be used as the burst test flow rate. Combinations of the burst test force values listed above can also be used.

One burst test force parameter can be measured during the burst test and converted into another burst test force parameter after the burst test. For instance, the processing unit 14 can monitor the pressure within the package 20 during the peel time. The processing unit 14 can apply Equation 1 to determine the average pressure within the package 20 during the peel time. Equation 1 can be easily adapted to measure a time average of other burst test force parameters. These burst test force parameter values can be monitored during the burst test and average values can be determined. Alternatively, one or more burst test force parameter values can be measured during a burst test and then converted to another burst test force parameter value for the purpose of determining an average.

Figure 4:
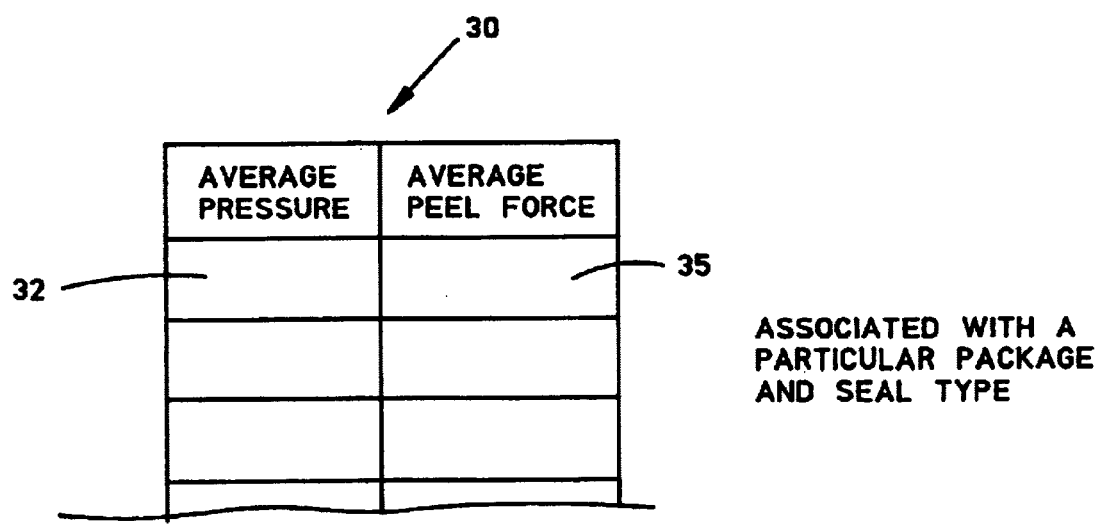
FIG. 4 illustrates a test conversion database.

A burst test force parameter can be compared to a test conversion relationship to convert results for a burst test to results for a peel test. The test conversion relationship can be expressed in a test conversion database 30 such as the database illustrated in FIG. 4. The test conversion database 30 includes burst test force parameter value fields 32 which are each associated with a peel test force parameter value field 35. Each burst test force parameter value field 32 lists a burst test force parameter value and each peel test force parameter value field 32 lists a peel test force parameter value. Each peel test force parameter value indicates the peel test force parameter value that would result from a peel test performed at the peel velocity that resulted from performing a burst test at the associated burst test force. The test conversion database 30 can be used to convert a burst test force parameter value to a peel test force parameter value. This conversion can be done by comparing a burst test force parameter value to the test conversion database 30 to find a peel test force parameter value associated with the burst test force parameter value. Interpolation and extrapolation can be employed when the experimental value for the burst test force parameter value is not listed in the test conversion database 30.

Figure 5:
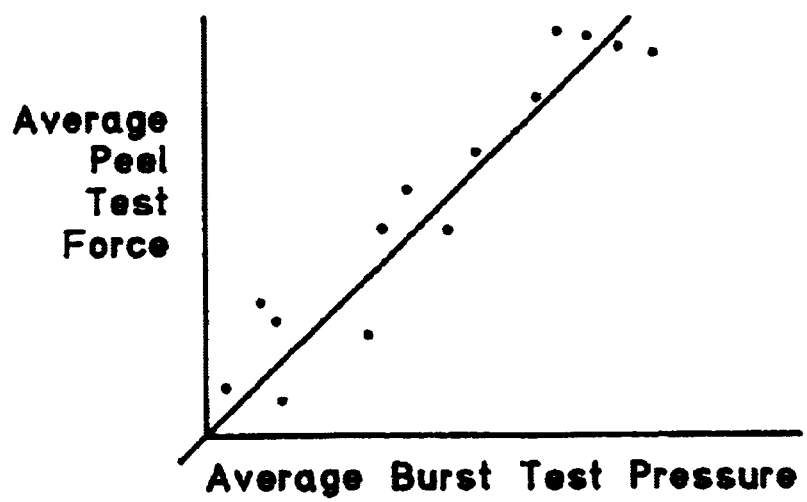
FIG. 5 illustrates a test conversion relationship expressed as a mathematical expression.

The test conversion relationship can also be expressed as a mathematical expression. For instance, a curve fit can be applied to the burst test force parameter value data versus the peel test force parameter value data. The resulting curve can serve as the test conversion relationship. For instance, FIG. 5 illustrates burst test force parameter values plotted against peel test force parameter values 32. Specifically, the average pressure measured during a burst test is plotted versus the average force measured during a peel test. A curve is fit to the data. The curve fit can be a continuous curve such as a linear curve fit or a discontinuous curve fit such as a step-wise function. The expression(s) that define the curve can serve as the test conversion relationship. The expression (s) for the curve illustrated in FIG. 5 would express the burst test force parameter value as a function of the peel test force parameter value. A burst test force parameter value can be converted to a peel test force parameter value by substituting the burst test force parameter value into the relationship.

The test conversion relationship can be experimentally generated. For instance, the test conversion relationship can be generated by performing a burst test at a constant pressure. A burst test force parameter value is determined along with the velocity that the seal 28 peels. A peel test is then performed at the determined peel velocity for seal 28 on either an undisturbed segment of the package or on a seal that was manufactured to have a seal quality that is substantially the same as the seal of the burst package. A peel test force parameter value is measured during the peel test. The burst test force parameter value and the peel test force parameter value are stored such that the burst test force parameter value is associated with the peel test force parameter value. For instance, the burst test force parameter value and the peel test force parameter value can be entered into a test conversion database 30 such as the database illustrated in FIG. 4. Additional data is generated by repeating the above steps beginning with performing additional burst tests at different constant pressures.

Figure 6:
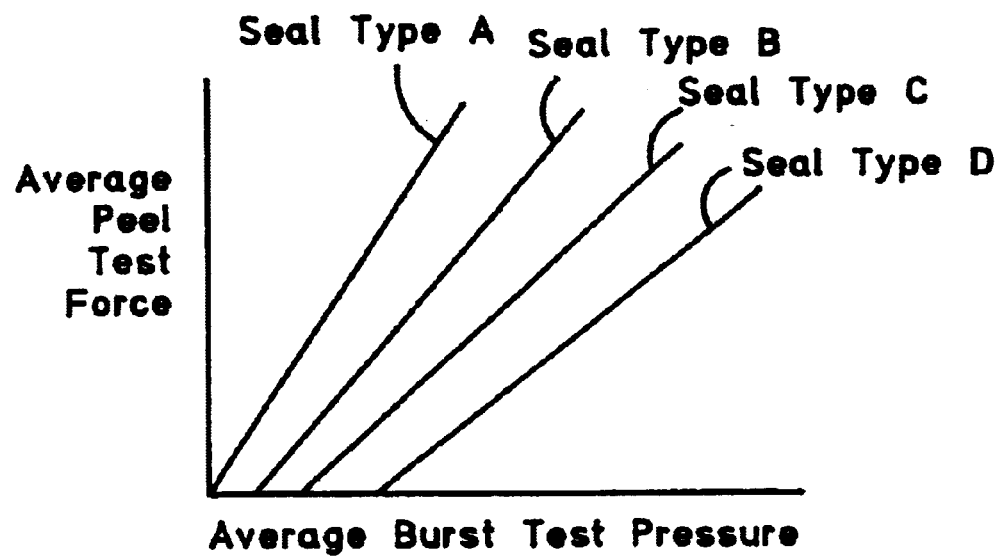
FIG. 6 illustrates test conversion relationships for different package types.

The test conversion relationship is generated for each type of package 20. Different package 20 types can include packages of different sizes and shapes. FIG. 6 illustrates test conversion relationships for different package 20 types. In particular, the average pressure during a burst test is plotted against the average force during a peel test. Because, a test conversion relationship is determined for each type of package 20, each test conversion relationship is associated with a package 20 type. When each test conversion relationship is expressed as a two dimensional database, the two dimensional databases can be arranged in a three dimensional test conversion database consisting of a plurality of two dimensional test conversion databases that are each associated with a different package type.

The peel test force parameter values 32 determined from the test conversion relationship can be compare with integrity evaluation data. The integrity evaluation data can include one or more integrity evaluation relationships that can be used in determining the integrity of a seal 28. An integrity evaluation relationship provides the relationship between the peel velocity and the peel test force parameter value for seals of a particular seal integrity.

Figure 7A:
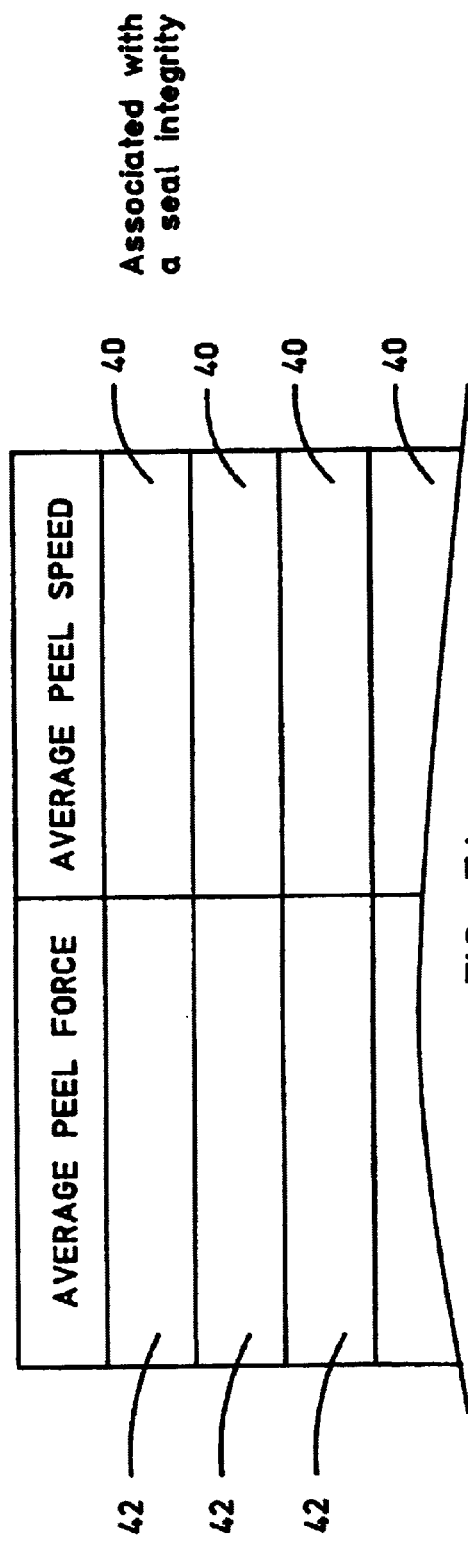
FIG. 7A illustrates an integrity evaluation database.

The integrity evaluation relationship can be expressed as an integrity evaluation database such as the database illustrated in FIG. 7A. The integrity evaluation database includes peel velocity value fields 40 that are each associated with a peel test force parameter value fields. Each test force parameter value field lists a peel test force parameter value that would result from a peel test performed at the peel velocity value listed in the associated peel velocity value field.

Figure 7B:
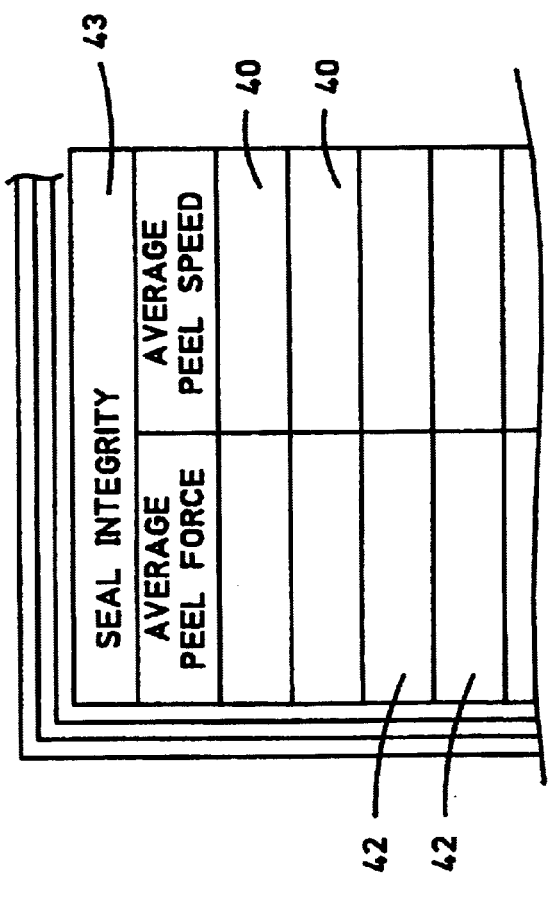
FIG. 7B illustrates a plurality of two dimensional integrity evaluation databases that are each associated with a seal integrity arranged in a three dimensional integrity evaluation database.

Because each integrity evaluation relationship is associated with seals of a particular integrity, each integrity evaluation database is associated with seals of a particular integrity. The integrity evaluation databases can be arranged in a three dimensional database as shown in FIG. 7B. The three dimensional integrity evaluation database includes a plurality of two dimensional integrity evaluation databases. Each of the two dimensional integrity evaluation databases is also associated with a seal integrity. Each two dimensional integrity evaluation database can include a seal integrity field 43 where the seal integrity associated with the two dimensional integrity evaluation database can be entered.

Figures 8, 9:
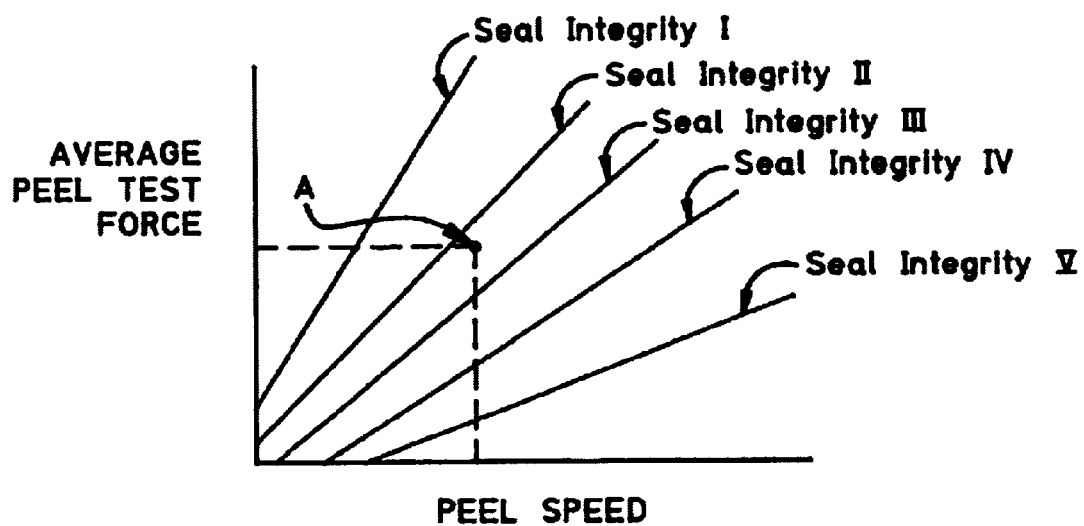
FIG. 8 illustrates peel test force parameter values plotted against peel velocity values for seals of a particular integrity.
FIG. 9 is a graphical representation of integrity evaluation data.

The integrity evaluation relationship can also be expressed as a mathematical expression. For instance, a curve fit can be applied to the peel test force parameter value versus the peel velocity data. The expression for the resulting curve can serve as the test conversion relationship. For instance, FIG. 8 illustrates peel test force parameter values 32 plotted against peel velocity values for seals of a particular integrity. Specifically, the average force measured during a peel test is plotted versus the average velocity during a peel test. A curve is fit to the data. The curve fit can be continuous such as a linear curve or a discontinuous curve such as a step-wise function. The expression(s) that define the curve can serve as the integrity evaluation relationship. The expression(s) for the curve illustrated in FIG. 8 would express the peel test force parameter value as a function of the peel velocity for a seal 28 of a particular integrity.

FIG. 9 is a graphical representation of integrity evaluation data. The peel test force parameter value is plotted against the average peel velocity for each seal integrity. More specifically, the average peel test force is plotted against the average peel velocity. Each of the curves is associated with a particular seal integrity.

The integrity evaluation data can be used to determine the seal integrity for a particular seal. For instance, a constant pressure burst test is performed on a package. A peel velocity and a burst test force parameter value can be determined. The burst test force parameter value is compared to the test conversion relationship to determine a peel test force parameter value. The determined peel test force and peel velocity are then compared to the integrity evaluation data to approximate the seal integrity for the package 20.

FIG. 9 illustrates approximation of the seal integrity for the package 20. The peel test force and peel velocity determined from a constant pressure burst test are shown as the point labeled A in FIG. 9. The point is positioned between a curve determined for seals of integrity II and a curve determined for seals of integrity III. Interpolation and/or other mathematical techniques can be used to approximate the integrity of a seal 28 at point A. Alternatively, the integrity of a seal 28 at point A can be rounded to the integrity of the curve that is nearest to the point or truncated to the integrity of the curve beneath the point or elevated to the integrity of the curve above the point.

Although FIG. 9 is used to illustrate a method for estimating the integrity, the method can be performed without using any graphical representation of data. For instance, the interpolation discussed above can be performed using the integrity evaluation databases without creating the graphical representation.

The integrity evaluation relationships can be experimentally generated. For instance, the integrity evaluation relationships can be generated by performing a series of peel tests on seals of a known integrity. A peel velocity and peel test force parameter value is determined for each peel test. The peel velocity and peel test force parameter value are stored such that the peel test force parameter value is associated with the peel velocity. For instance, the peel test force parameter value and the peel velocity can be entered into an integrity evaluation database such as the database illustrated in FIG. 7A. Additional integrity evaluation databases can be generated by repeating the above steps on seals of a different integrity. The integrity evaluation databases can be arranged in a three dimensional integrity evaluation database with seal integrity providing the third dimension.

Figure 10:
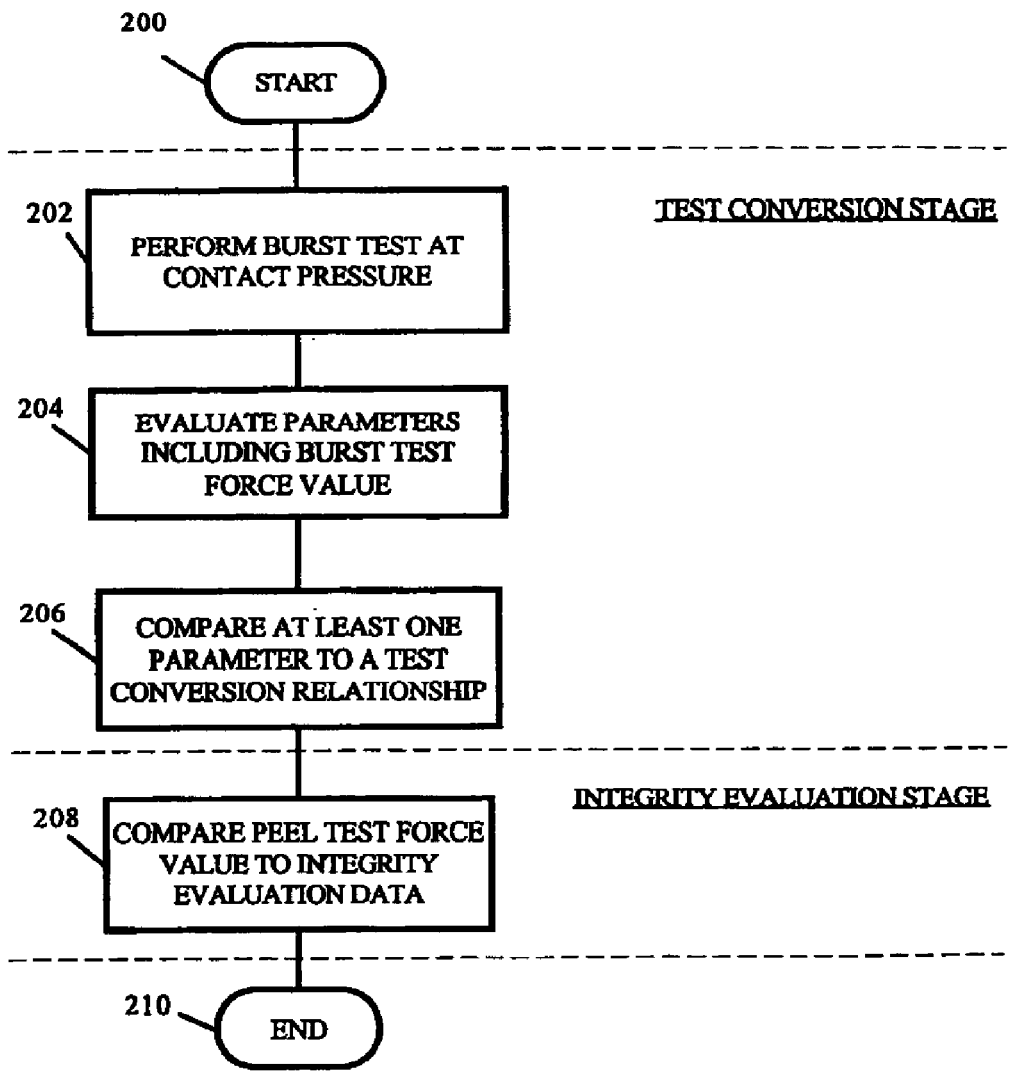
FIG. 10 illustrates a method of evaluating the results of a burst test.

FIG. 10 illustrates a method of evaluating the results of performing a burst test on a package. The method includes a test conversion stage and an integrity evaluation stage. The test conversion stage includes converting the results of the burst test so they can be compared with the results of a peel test. For instance, the test conversion stage can include converting a burst test force parameter value to a peel test force parameter value. The integrity evaluation stage includes using a result of the test conversion stage to evaluate the integrity of the seal. The integrity evaluation can be measured by a peel test. Accordingly, the results of each stage of the method can be compared with peel test results.

The method illustrated in FIG. 10 begins at start block 200. A constant pressure burst test is performed on a package 20 at process block 202. A variety of parameters are evaluated at process block 204. The evaluated parameters are each a function of the value of each parameter changes as the seal 28 changes. Suitable parameters include, but are not limited to, peel velocity, seal width and peel time. The evaluated parameters can also include one or more burst test force parameter values such as pressure as a function of time during the peel time, average pressure during the peel time. The parameters can be evaluated before, during or after the burst test. For instance, the seal width can be measured before the burst test is performed while the pressure is evaluated during the burst test.

At least one burst test force parameter value is compared to a test conversion relationship at process block 206 to determine a peel test force parameter value. The peel test force parameter value is a force parameter value that can be directly compared to peel test results. As described above, a suitable burst test force parameter value is average pressure during the peel time. The average pressure can be compared to a test conversion database 20 to determine an average peel test force that is directly comparable to average force parameter values for peel test performed on the same package.

The peel test force parameter value generated at process block 206 is compared to integrity evaluation data at process block 208. The comparison provides an integrity for a seal 28 on the package 20 that is comparable to seal 28 integrities measured with a peel test. A suitable method for comparing the peel test force parameter value with the integrity evaluation data is illustrated in FIG. 9 and the accompanying description. The method ends at end block 210.

Figure 11:
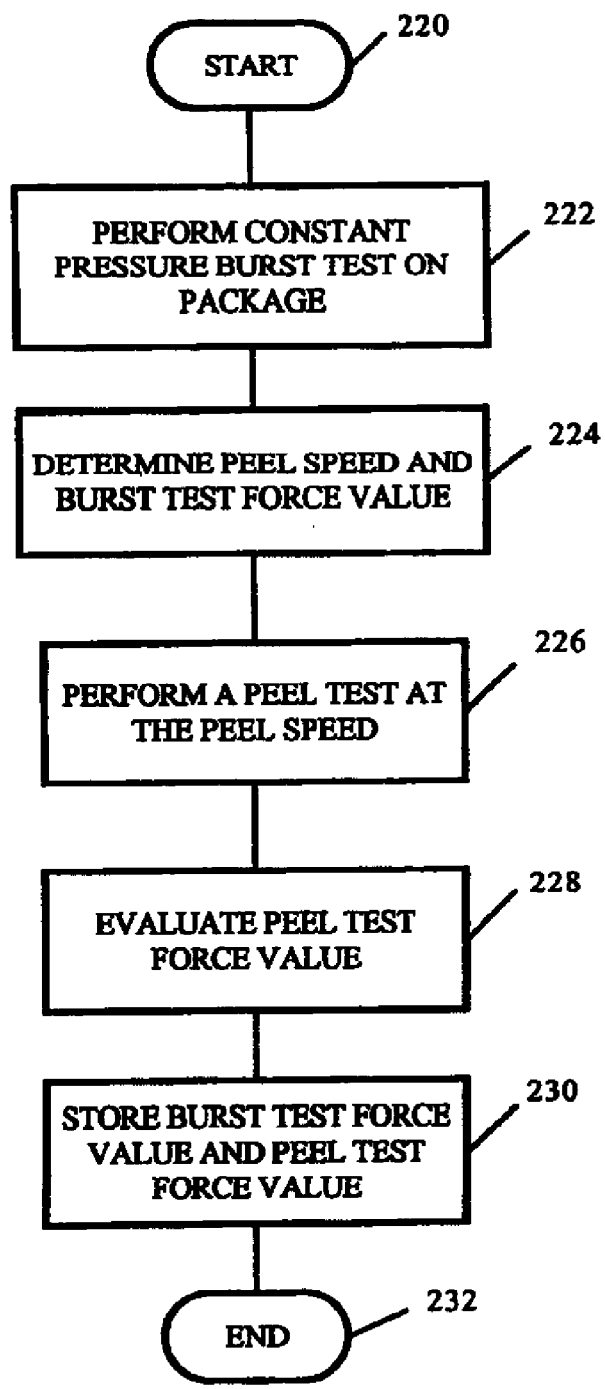
FIG. 11 illustrates a method of generating data for a test conversion database.

FIG. 11 illustrates a method of generating data for a test conversion database 30. The method begins at start block 220. A constant pressure burst test is performed on a particular package type having a particular seal 28 type at process block 222.

A variety of parameters including at least the peel velocity and one or more burst test force parameter values are evaluated at process block 224. A suitable burst test force parameter value includes, but is not limited to, the average pressure during the peel. The parameters can be evaluated before, during or after the burst test. For instance, the seal width can be measured before the burst test while the peel time is evaluated during the burst test. The seal width can be divided by the peel time to determine the peel velocity.

A peel test is performed at process block 226. The peel test is performed at the peel velocity evaluated at process block 224 on either an undisturbed segment of the package or on a seal that was manufactured to have a seal quality that is substantially the same as the seal of the burst package. One or more peel test force parameter values 32 are evaluated at process block 228. A suitable peel test force parameter value includes, but is not limited to, the average force during the peel. The burst test force parameter values and the peel test force parameter value are stored at process block 230. The burst test force parameter value and the peel test force parameter value are stored such that the burst test force parameter value is associated with the peel test force parameter value. For instance, the burst test force parameter value and the peel test force parameter value can be stored in a row of the test conversion database 30 illustrated n FIG. 4. Storing the data can include storing the data in the machine readable medium. The method terminates at end block 232.

As described above, the method illustrated in FIG. 11 includes performing a burst test at a constant pressure. Additional data can be generated for the test conversion database 30 by repeating the method of FIG. 11 at different pressures.

As described above, each test conversion database 30 is associated with a particular package 20 type. Accordingly, when the method of FIG. 11 is performed on packages having the same geometry, the generated data can be stored in the same test conversion database 30.

Figure 12:
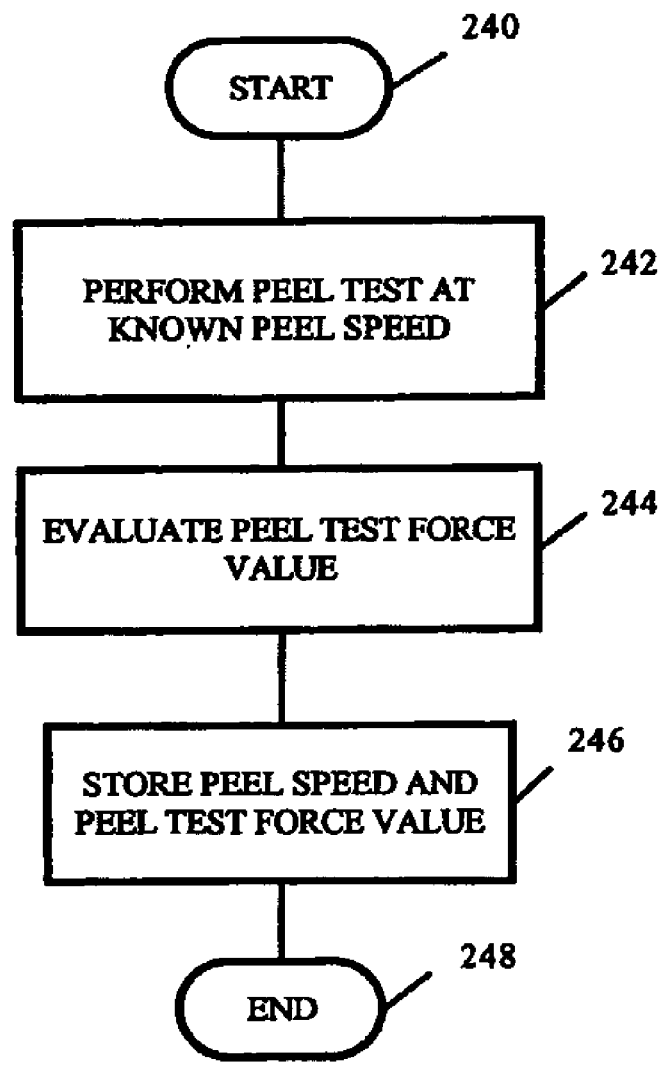
FIG. 12 illustrates a method of generating integrity evaluation data.

FIG. 12 illustrates a method of generating integrity evaluation data. The method starts at start block 240. A peel test is performed on a seal 28 of a known integrity at process block 242. The peel test is performed at a particular peel velocity. A peel test force parameter value is evaluated at process block 244. The peel test force parameter value can be evaluated before or after the peel test is performed. The peel test force parameter value and the peel velocity are stored at process block 246. The peel test force parameter value and the peel velocity are stored such that the peel 2 test force parameter value is associated with the peel velocity and with the integrity of the seal 28. For instance, the peel test force parameter value and the peel velocity can be stored in the same row of an integrity evaluation database that is associated with the integrity of the tested seal 28 such the integrity evaluation database of FIG. 7A. The method terminates at end block 248.

As described above, the method illustrated in FIG. 12 includes performing a peel test at a particular velocity. Additional data for an integrity evaluation database can be generated by repeating the method of FIG. 12 at a different velocity. As described above, each integrity evaluation database is associated with a particular seal integrity. Accordingly, when the method of FIG. 12 is performed on seals having the same integrity, the generated data can be stored in the same integrity evaluation database.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

What is claimed is:

1. A method for evaluating a seal on a package, comprising:

determining a value of a burst test force parameter, the burst test force parameter being a parameter that results from a force placed on the package during a burst test; and using the value of the burst test force parameter to determine a value of a peel test force parameter for the package, the peel test force parameter being a parameter that results from a force placed on the package during a peel test;

wherein using the value of the burst test force parameter to determine a value of a peel test force parameter includes;

comparing the burst test force parameter value to a test conversion relationship associating burst test force parameter values and peel test force parameter values, the association indicating the burst test force parameter value and the peel test force parameter value that would result from performing a burst test and a peel test such that a seal would peel at substantially the same velocity during the burst test and during the peel test.

2. The method of claim 1, wherein the relationship is expressed as a database including a plurality of peel test force parameter values that are each associated with a burst test force parameter value.

3. The method of claim 1, wherein the relationship is expressed as a mathematical expression.

4. The method of claim 1, wherein the burst test is a constant pressure burst test.

5. The method of claim 1, further comprising:

determining the velocity at which the seal peels during the burst test.

6. The method of claim 1, further comprising:

using the value of the burst test force parameter to determine an integrity for the seal, the integrity being generated from a peel test.

7. The method of claim 1, further comprising:

comparing the determined value of the peel test force parameter to integrity evaluation data.

8. The method of claim 7, wherein the integrity evaluation data includes a plurality of integrity evaluation relationships that provide a relationship between peel velocity and the peel test force parameter value, each integrity evaluation relationship being associated with a particular seal integrity.

9. The method of claim 1, further comprising:

determining the velocity at which the seal peels during the burst test; and comparing the determined value of the peel test force parameter and the determined peel velocity to integrity evaluation data.

10. The method of claim 1, wherein the burst test force parameter value is selected from the group consisting of: pressure, work, force, power and rate of fluid inflow.

11. The method of claim 1, wherein the peel test force parameter value is selected from the group consisting of work, force and power.

12. A method for evaluating a seal on a package, comprising:
- evaluating a value of a burst test force parameter, the burst test force parameter being a parameter that results from a force placed on the package during a burst test; and
- using the value of the burst test force parameter to determine a seal integrity, the seal integrity being an integrity value that is determined by performing peel tests on the seal;
- wherein using the value of the burst test force parameter to determine a peel test seal integrity for the seal includes;
- using the value of the burst test force parameter to determine a value of a peel test force parameter for the package; and
- comparing the value of the peel test force parameter to seal integrity evaluation data.

13. The method of claim 12, wherein the integrity evaluation data includes a plurality of integrity evaluation relationships that provide a relationship between peel velocity and the peel test force parameter value, each integrity evaluation relationship being associated with a particular seal integrity.

14. The method of claim 13, further comprising:
- determining the velocity at which the seal peels during the burst test; and
- comparing the determined peel velocity, and the value of the peel test force parameter to one or more of the integrity evaluation relationships.

15. The method of claim 12, wherein the burst test includes a constant pressure burst test.

16. The method of claim 12, wherein the burst test force parameter value is selected from the group consisting of: pressure, work, force, power and rate of fluid inflow.

17. A method of preparing data for use with a seal testing device, comprising:
- performing a burst test and a peel test such that a type of seal on a type of package peels at substantially the same velocity during the peel test and the burst test;
- evaluating a burst test force parameter value that results from a force applied to the package during the burst test;
- evaluating a peel test force parameter value that results from a force applied to the package during the peel test; and
- storing the value of the burst test force parameter such that it is associated with the value of the peel test force parameter.

18. The method of claim 17, wherein storing the value of the burst test force parameter such that it is associated with the value of the peel test force parameter includes
- storing the value of the burst test force parameter and the value of the peel test force parameter in a database.

19. The method of claim 18, wherein the database is associated with the seal type and the package type.

20. The method of claim 17, wherein storing the value of the burst test force parameter such that it is associated with the value of the peel test force parameter includes
- storing the value of the burst test force parameter and the value of the peel test force parameter in a machine readable medium.

21. The method of claim 17, wherein the burst test force parameter value is selected from the group consisting of: pressure, work, force, power and rate of inflow.

22. The method of claim 17, wherein the peel test force parameter value is selected from the group consisting of work, force and power.

23. A method of preparing data for use with a seal testing device, comprising:
- performing a plurality of peel tests on packages that each have the same seal integrity rating, each peel test performed at a different peel velocity;
- evaluating a peel test force parameter value resulting from each peel test; and
- storing the peel test force parameter values such that the peel test force parameter value for a particular peel test is associated the with the peel velocity at which the particular peel test was performed.

24. A method for evaluating a seal on a package, comprising:
- determining a value of a burst test force parameter, the burst test force parameter being a parameter that results from a force placed on the package during a burst test;
- using the value of the burst test force parameter to determine a value of a peel test force parameter for the package, the peel test force parameter being a parameter that results from a force placed on the package during a peel test; and
- determining the velocity at which the seal peels during the burst test.

25. The method of claim 24, wherein using the value of the burst test force parameter to determine a value of a peel test force parameter includes comparing the burst test force parameter value to a test conversion relationship associating burst test force parameter values and peel test force parameter values, the association indicating the burst test force parameter value and the peel test force parameter value that would result from performing a burst test and a peel test such that a seal would peel at substantially the same velocity during the burst test and during the peel test, and the relationship is expressed as a database including a plurality of peel test force parameter values that are each associated with a burst test force parameter value.

26. The method of claim 24, wherein using the value of the burst test force parameter to determine a value of a peel test force parameter includes comparing the burst test force parameter value to a test conversion relationship associating burst test force parameter values and peel test force parameter values, the association indicating the burst test force parameter value and the peel test force parameter value that would result from performing a burst test and a peel test such that a seal would peel at substantially the same velocity during the burst test and during the peel test, and the relationship is expressed as a mathematical expression.

27. The method of claim 24, wherein the burst test is a constant pressure burst test.

28. The method of claim 24, further comprising:
- determining the velocity at which the seal peels during the burst test.

29. The method of claim 24, further comprising:
- using the value of the burst test force parameter to determine an integrity for the seal, the integrity being generated from a peel test.

30. The method of claim 24, further comprising:
- comparing the determined value of the peel test force parameter to integrity evaluation data.

31. The method of claim 30, wherein the integrity evaluation data includes a plurality of integrity evaluation relationships that provide a relationship between peel velocity and the peel test force parameter value, each integrity evaluation relationship being associated with a particular seal integrity.

32. The method of claim 24, further comprising:
comparing the determined value of the peel test force parameter and the determined peel velocity to integrity evaluation data.

33. The method of claim 24, wherein the burst test force parameter value is selected from the group consisting of power pressure, work, force, power and rate of fluid inflow.

34. The method of claim 24, wherein the peel test force parameter value is selected from the group consisting of work, force and power.

* * * * *

UNITED STATES PATENT AND TRADEMARK OFFICE
CERTIFICATE OF CORRECTION

PATENT NO. : 6,763,728 B1
DATED : July 20, 2004
INVENTOR(S) : Albrecht

It is certified that error appears in the above-identified patent and that said Letters Patent is hereby corrected as shown below:

Drawings,
Add Figures 10, 11 and 12 as attached.

Column 16,
Line 1, change claim 33 to read:
-- 33. The method of claim 24, wherein the burst test force parameter value is selected from the group consisting of: pressure, work, force, power and rate of fluid inflow. --

Signed and Sealed this

Fifteenth Day of February, 2005

JON W. DUDAS
*Director of the United States Patent and Trademark Office*